(12) United States Patent
Nakasawa et al.

(10) Patent No.: US 9,989,550 B2
(45) Date of Patent: Jun. 5, 2018

(54) AUTOMATED ANALYZING APPARATUS

(71) Applicant: HITACHI HIGH-TECHNOLOGIES CORPORATION, Tokyo (JP)

(72) Inventors: Takashi Nakasawa, Tokyo (JP); Yoshihiro Suzuki, Tokyo (JP); Yoichi Aruga, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 100 days.

(21) Appl. No.: 14/762,928

(22) PCT Filed: Dec. 20, 2013

(86) PCT No.: PCT/JP2013/084293
§ 371 (c)(1),
(2) Date: Jul. 23, 2015

(87) PCT Pub. No.: WO2014/119172
PCT Pub. Date: Aug. 7, 2014

(65) Prior Publication Data
US 2015/0369833 A1 Dec. 24, 2015

(30) Foreign Application Priority Data
Jan. 29, 2013 (JP) ................................ 2013-014710

(51) Int. Cl.
*G01N 35/10* (2006.01)
*G01N 35/00* (2006.01)

(52) U.S. Cl.
CPC ..... *G01N 35/1009* (2013.01); *G01N 35/0092* (2013.01); *G01N 35/00663* (2013.01);
(Continued)

(58) Field of Classification Search
CPC ......... G01N 35/1009; G01N 35/00663; G01N 35/00722; G01N 35/0092; G01N 35/1002
See application file for complete search history.

(56) References Cited

U.S. PATENT DOCUMENTS

| 2005/0175503 A1 | 8/2005 | Shiba et al. |
| 2005/0207938 A1 | 9/2005 | Hanawa et al. |
| 2012/0020838 A1 | 1/2012 | Mimura et al. |

FOREIGN PATENT DOCUMENTS

| JP | 2005-27171 A | 1/2005 |
| JP | 2005-37171 A | 2/2005 |

(Continued)

OTHER PUBLICATIONS

International Preliminary Report on Patentability received in corresponding International Application No. PCT/JP2013/084293 dated Aug. 13, 2015.
(Continued)

*Primary Examiner* — Jill A Warden
*Assistant Examiner* — Matthew D Krcha
(74) *Attorney, Agent, or Firm* — Mattingly & Malur, PC

(57) ABSTRACT

In an automated analyzing apparatus, problems arise when a reagent container is carried in during analysis, since it is necessary to stop all accesses of mechanisms etc. to a location of the apparatus where the reagent container is placed and, in a situation in which measurements have been already started, it is impossible to carry the reagent container after waiting about several minutes. To address the problems, when a remaining amount of a reagent corresponding to a predetermined item becomes equal to or less than a first threshold value, a pause cycle of reagent suction is generated in which the reagent dispensing mechanism does not suction the reagent from inside of a reagent container of a reagent disc at regular intervals, and a reagent container containing the same kind of reagent in the reagent disc by the reagent container carrying mechanism is automatically carried in the pause cycle.

7 Claims, 5 Drawing Sheets

(52) U.S. Cl.
CPC ... *G01N 35/00722* (2013.01); *G01N 35/1002* (2013.01); *G01N 2035/0094* (2013.01); *G01N 2035/00673* (2013.01); *G01N 2035/00891* (2013.01); *G01N 2035/1025* (2013.01); *G01N 2035/1051* (2013.01)

(56) References Cited

FOREIGN PATENT DOCUMENTS

| | | |
|---|---|---|
| JP | 2005-214683 A | 8/2005 |
| WO | 2010/117044 A1 | 10/2010 |

OTHER PUBLICATIONS

International Search Report of PCT/JP2013/084293.

[FIG. 1]
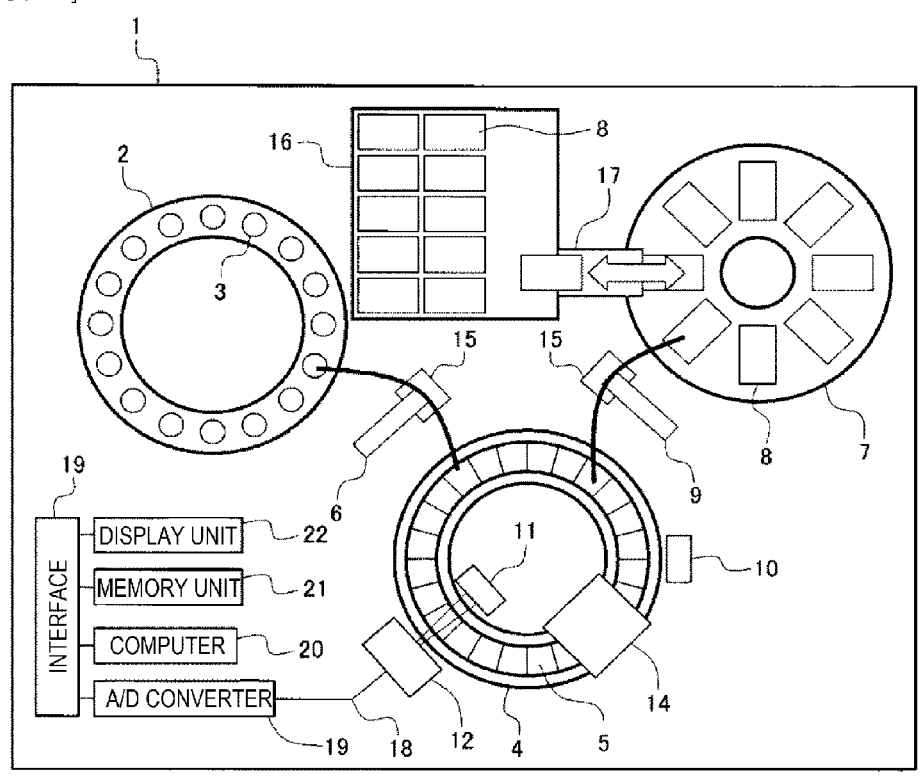

[FIG. 2]
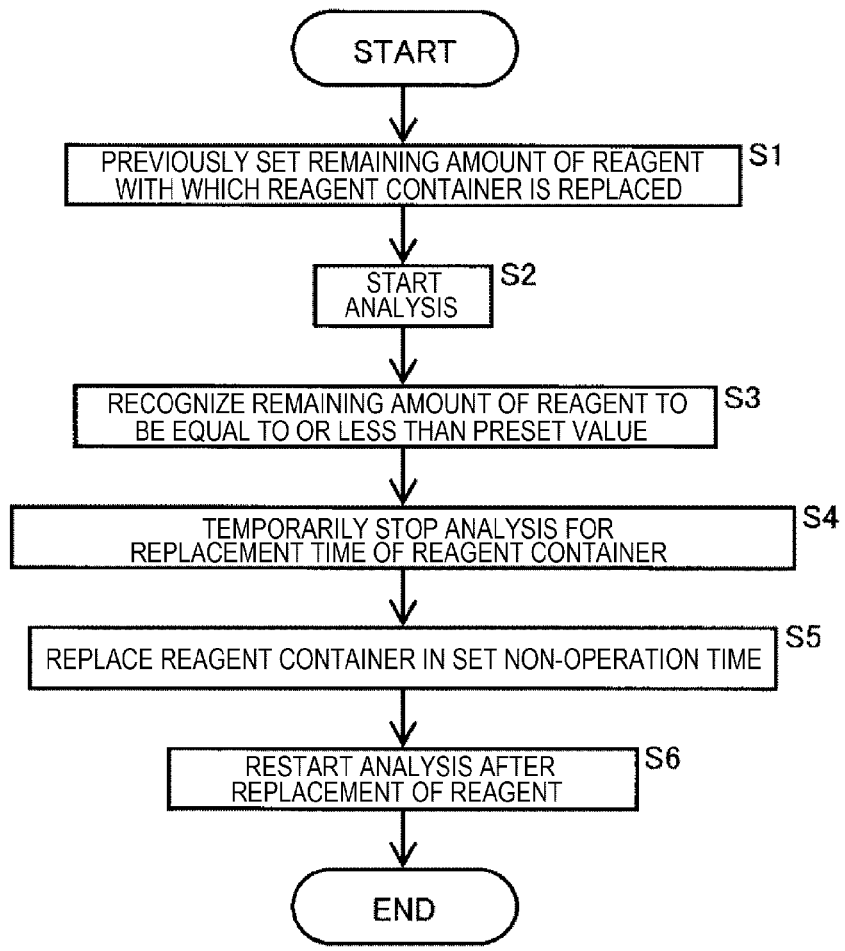

[FIG. 3]

| ITEM ALLOCATED ORDER | ITEM | NUMBER OF REMAINING TESTS | OPERATION CYCLE |||||||||||||||||||||||||
|---|---|---|---|---|---|---|---|---|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
| 1 | A | 7 | S | R1 | | | | | | | | | | | | | | | | | | | | | | | | |
| 2 | B | 100 | | S | R1 | | | | R2 | | | | | | | | | | | | | | | | | | |
| 3 | A | 6 | | | S | R1 | | | | | | | | | | | | | | | | | | | | | |
| 4 | B | 99 | | | | S | R1 | | | R2 | | | | | | | | | | | | | | | | | |
| 5 | A | 5 | | | | | S | R1 | | | | | | | | | | | | | | | | | | | |
| 6 | B | 98 | | | | | | S | R1 | | R2 | | | | | | | | | | | | | | | | |
| 7 | A | 4 | | | | | | | S | R1 | | | | | | | | | | | | | | | | | |
| 8 | B | 97 | | | | | | | | S | R1 | | R2 | | | | | | | | | | | | | | |
| 9 | A | 3 | | | | | | | | | S | R1 | | | | | | | | | | | | | | | |
| 10 | (SPARE) FOR REAGENT LOADING | | | | | | | | | | | | | | | | | | | | | | | | | | |
| 11 | B | 96 | | | | | | | | | | S | R1 | | R2 | | | | | | | | | | | | |
| 12 | A | 2 | | | | | | | | | | | | S | R1 | | | | | | | | | | | | |
| 13 | B | 95 | | | | | | | | | | | | | S | R1 | | R2 | | | | | | | | | |
| 14 | A | 1 | | | | | | | | | | | | | | S | R1 | | | | | | | | | | |
| 15 | (SPARE) FOR REAGENT LOADING | | | | | | | | | | | | | | | | | | | | | | | | | | |
| 16 | (SPARE) CHECK AMOUNT OF LOADED REAGENT (FIRST REAGENT CONTAINER) | | | | | | | | | | | | | | | | | | R2 | R2 | | | | | | | | |
| 17 | (SPARE) CHECK AMOUNT OF LOADED REAGENT (SECOND REAGENT CONTAINER) | | | | | | | | | | | | | | | | | | | | S | R1 | R1 | R1 | | | | |
| 18 | B | 94 | | | | | | | | | | | | | | | | | | | S | R1 | | R2 | | | |
| 19 | A | 100 | | | | | | | | | | | | | | | | | | | | | S | R1 | | | | |
| 20 | B | 93 | | | | | | | | | | | | | | | | | | | | | | S | R1 | | R2 | R2 |

NUMBER OF TESTS ≤ X

<< 1. REGISTRATION OPERATION OF NEW REAGENT CASSETTE

CARRY-IN OPERATION OF ITEM A REAGENT CONTAINER
CHECK OPERATION OF AMOUNT OF LOADED ITEM A REAGENT (FIRST REAGENT)
CHECK OPERATION OF AMOUNT OF LOADED ITEM A REAGENT (SECOND REAGENT)

[FIG. 4]
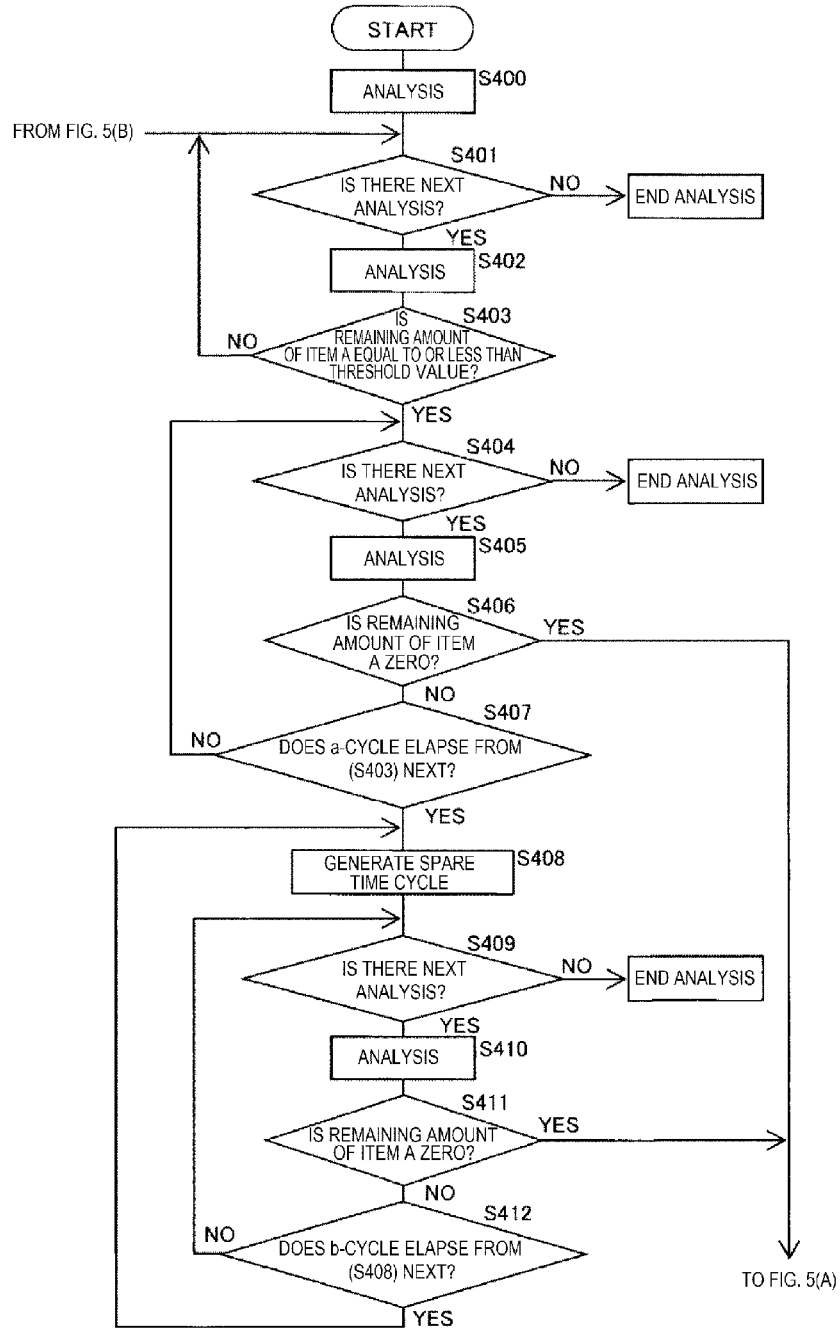

[FIG. 5]
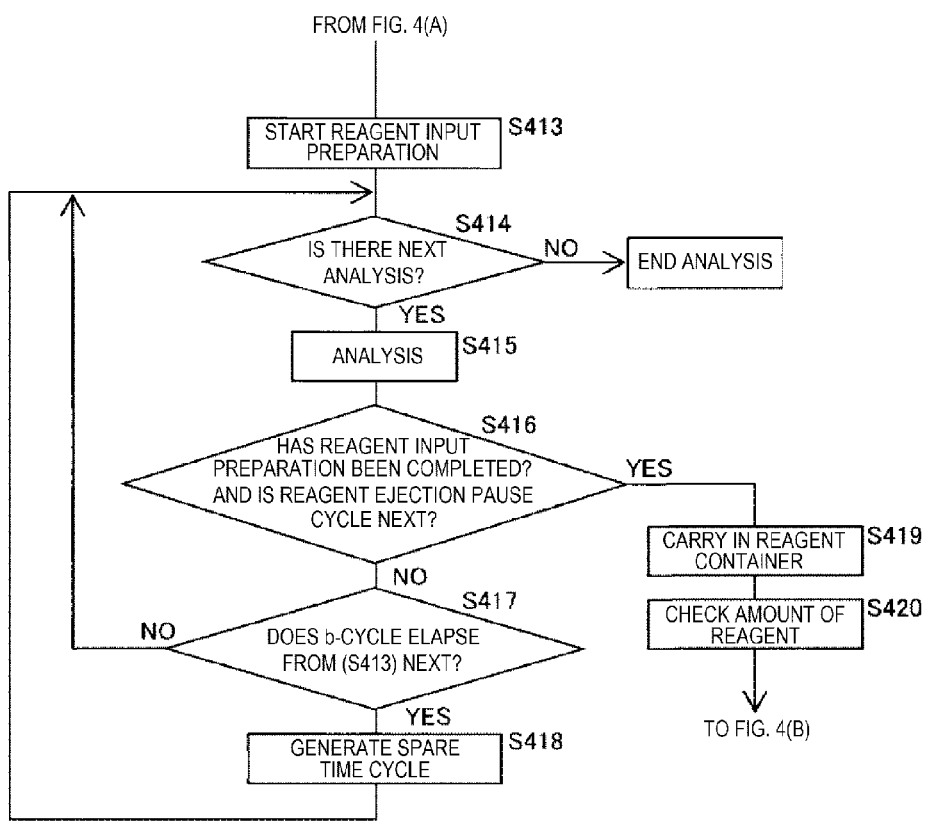

AUTOMATED ANALYZING APPARATUS

TECHNICAL FIELD

This invention relates to an analyzing apparatus for clinical laboratory test for qualitative and quantitative analyses of biological samples such as blood and urine, and specifically to an automated analyzing apparatus having a function of automatically supplying samples and reagents necessary for measurements to the apparatus.

BACKGROUND ART

In an analyzing apparatus for clinical laboratory test, measurements of specific components in biological samples such as blood and urine are performed. As a general operation, the sample is dispensed from a sample container to a reaction container using a dedicated nozzle, then, dispensing is performed from a reagent container into the reaction container to which the sample has been dispensed using a dedicated nozzle and they are stirred, and then, they are reacted in certain time and concentration calculation of a target item is performed from information of absorbance and an amount of luminescence obtained from a reaction liquid. The reagents used for measurements are loaded in the reagent containers in certain volumes, and the used reagent containers are discarded or replenished with another reagent and used. Recently, in view of prevention of medical malpractice such as a measurement mistake due to a loading mistake of a reagent and setting of a reagent container for another item in a location in which a reagent container should be set (i.e., misplacement), the containers have been respectively managed using traceable indicators such as barcodes, and the used containers have not been replenished with reagents for prevention of deterioration of reagents as much as possible, but have been disposable.

Generally, after completion of measurements of the day, an operator manually calculates an amount of a reagent necessary until the end time of the next day and set in the apparatus. Of reagents, a plurality of reagents may be used for one item, and one or more hour may be taken for confirmation of insufficient reagents, taking out of necessary reagents from a refrigerator, and setting in the apparatus.

Recently, one automated analyzing apparatus has been often used night and day. However, an operator using the apparatus in a night shift is not necessarily a person in charge of the automated analyzing apparatus, and a person in a day shift generally undertakes all of reagent replacement works and other maintenance of the apparatus. Further, in the 24-hour operation, if the maintenance takes time, subsequent tests may be delayed by the time, and thus, reduction of the requirement of the time-consuming maintenance of reagent replacement or the like is requested.

Currently, an apparatus having a function of placing reagents in another location on the apparatus in advance, and automatically loading reagent containers in locations in which the reagents should be placed while monitoring the remaining amounts of the reagents during use is developed. However, when the used-up reagent is newly added, the sample measurement should be stopped for several minutes. In emergencies and busy hours of measurements, the function is not necessarily effective and the more efficient automatic reagent supply and eject function is required.

CITATION LIST

Patent Literature

PTL 1: JP-A-2005-214683

SUMMARY OF INVENTION

Technical Problems

The number of operators in a clinical site such as clinical laboratory technologists is minimized with the trend of medical cost reduction, single technologist is extremely busy undertaking a plurality of practices. The busy practices include the maintenance of the apparatus, reagent replacement (hereinafter, replacement includes only reagent carry-in), calibration curve control, accuracy control, etc. Accordingly, under the present circumstances, reduction of the number of maintenances that the operator should actually perform is required.

In an automated analyzing apparatus, after dispensing of a sample, it is necessary to dispense a plurality of reagents in a certain period. In most automated analyzing apparatuses, the first reagent is dispensed and, five minutes later, the next reagent is dispensed. The period is a very important factor in measurement reaction and it is impossible to change the period to dispensing of the second reagent for accurate analysis.

As described above, for reduction of reagent replacement work by the operator, an apparatus having a function of automatically placing reagent containers in locations of the apparatus in which the reagents should be placed has been launched. When the reagent containers are actually loaded, a certain time is taken for carrying the reagent container from a location for temporary storage to a location in which the container is to be placed. Accordingly, for replenishment work of reagent containers, the operator should wait a time for stopping dispensing of the sample to ejection of the last reagent for the analysis on which a measurement request is currently sent to the apparatus. Particularly, in hours of many test requests, the function is not necessarily a significant function in reality. PTL 1 describes a function of giving an instruction of replenishment of reagent containers to the apparatus in advance, and stopping dispensing for analysis for a designated time and displaying a time till when the reagent containers can be loaded on a screen of the apparatus or the like. The invention enables replenishment of reagent containers without decreasing the original processing power of the apparatus by performing the replenishment work of reagent containers intermittently required with a will of operator's own. However, the work and confirmation by the operator are required and reagent replacement may not be executed until completion of all of the required reagent dispensing with respect to the items that have already been requested for analysis. Therefore, reduction of burden on workers and prompt analyses have not yet realized.

The invention has been achieved in view of the above described problems, and an object of the invention is to provide an automated analyzing apparatus that can automatically place reagent containers in designated location by which a remaining amount within a reagent container during use is monitored, dispensing of a sample or a reagent associated with the sample is stopped for a period necessary for carrying the reagent container in a designated location at a time when the remaining amount is an arbitrary set amount, and thereby, the analysis stop time of the apparatus for carrying in and out of the reagent container may be minimized.

Solution to Problems

In order to achieve the object, the invention includes a reaction disc on which a reaction container for reaction of a sample and a reagent is mounted, alight source that applies light to the reaction container, a photometer that senses the light applied to the reaction container, a reagent disc on which a reagent container containing the reagent used for the reaction is placed, a reagent storage that stores the reagent container containing the reagent, a reagent container carrying mechanism that carries the reagent container from the reagent storage to the reagent disc, a reagent dispensing mechanism that suctions the reagent from the reagent container placed on the reagent disc and ejects the reagent to the reaction container, a sample dispensing mechanism that ejects the sample to the reaction container, and a control unit that controls the reagent dispensing mechanism and the reagent container carrying mechanism, wherein the control unit performs control, when a remaining amount of a reagent corresponding to a predetermined item becomes equal to or less than a first threshold value, of generating a pause cycle of reagent suction in which the reagent dispensing mechanism does not suction the reagent from inside of the reagent container of the reagent disc at regular intervals, and automatically carrying a reagent container containing the same kind of reagent as the reagent corresponding to the predetermined item in the reagent disc by the reagent container carrying mechanism in the pause cycle.

Advantageous Effects of Invention

The invention can monitor a remaining amount of a reagent during use when automatically carrying in the reagent, at the time when the remaining amount becomes a preset amount, stop ejection operation of the reagent in a period necessary for reagent carry-in in advance, and thereby, minimize the stop time of an analysis due to the reagent carry-in. Further, the invention can make the time to reagent carry-in shorter when the reagent carry-in is truly necessary by generating a pause cycle in which the reagent is not suctioned at regular intervals.

BRIEF DESCRIPTION OF DRAWINGS

FIG. 1 shows a top layout of a main part of an automated analyzing apparatus with the addition of a conceptual diagram of a control system according to the invention.

FIG. 2 is a reagent container replacement flow chart of the invention.

FIG. 3 is a conceptual diagram showing one example of a reagent container replacement schedule of the invention.

FIG. 4 is a control flow chart of the invention.

FIG. 5 is the control flowchart of the invention.

DESCRIPTION OF EMBODIMENTS

As below, an automated analyzing apparatus for clinical laboratory test according to one embodiment of the invention and its function will be explained using FIGS. 1 to 5.

First, one example of the automated analyzing apparatus to which the invention is applied will be explained by taking FIG. 1 as an example. FIG. 1 shows a top layout of a main part of an automated analyzing apparatus with the addition of a conceptual diagram of a control system. The target automated analyzing apparatus of the invention has a mechanism of collecting liquids of samples, reagents, etc. using dispensing nozzles in predetermined amounts. As below, the explanation will be made by an automated analyzing apparatus for clinical laboratory test that performs analyses of biological samples including blood, urine, etc. as an example. However, the invention is not limited to that, but includes a rack system in which the sample is carried to an analysis unit using a sample rack or a robot handling system in movement of reagent containers.

An automated analyzing apparatus 1 includes a sample disc 2, a sample container 3 coaxially provided with the disc, a reaction disc 4, a reaction container 5 coaxially provided with the disc, a sample dispensing mechanism 6, a reagent container 8 coaxially provided with a first reagent disc 7 and containing various reagents, a reagent dispensing mechanism 9, a stirring mechanism 10, a light source 11, a photometer (multi-wavelength photometer) 12, an A/D converter 13, a reaction container cleansing mechanism 14, a dispensing nozzle cleansing mechanism 15, a second reagent storage 16, and a reagent container carrying mechanism 17.

An analysis using the automated analyzing apparatus 1 is performed in the following sequence. First, the sample dispensing mechanism 6 dispenses an analyte sample from the sample container 3 to the reaction container 5. Then, the reagent dispensing mechanism 9 dispenses a reagent used for the analysis from the reagent container 8 to the reaction container 5. Subsequently, a liquid mixture is stirred by the stirring mechanism 10. Light emitted from the light source 11 and transmitted through the reaction container 5 containing the liquid mixture is sensed and measured by the photometer (multi-wavelength photometer) 12 and transmitted to an interface 19 via the A/D converter 13. A computer 20 has a function as a control unit, and results obtained from calculations by the control unit are saved in memory means 21 and output to an information apparatus and, for example, displayed on a display unit 22. In a position where the reagent container is not placed within the first reagent disc 7, a new reagent container 8 is placed from the second reagent storage 16 by the reagent container carrying mechanism 17 with a need. Or, without a need or when the reagent container 8 is discarded, the reagent container is moved into the second reagent storage by the reagent container carrying mechanism 17. The dispensing nozzle cleansing mechanism 15 cleanses the end of the dispensing nozzle at each time when the sample dispensing mechanism 6 and the reagent dispensing mechanism 9 dispense the sample or reagent. Further, the reaction container 5 after reaction is cleansed by the reaction container cleansing mechanism 14 and repeatedly used for the next reaction. All of the operation mechanisms of the analyzing apparatus are controlled by the control unit contained in the computer 20 via communication means 18 and the interface 19. Note that any photometer that senses not only absorbance, but light applied to the reaction container such as scattering luminosity may be used.

Details of times of the above described movement from the first reagent disc to the second reagent storage will be explained using FIGS. 2 and 3.

In FIGS. 2 and 3, the explanation is made by taking an operation when two reagent discs are used on the automated analyzing apparatus shown in FIG. 1 as an example. Note that the first reagent disc and the second reagent storage are not necessarily located in the same one analyzing apparatus, but may be provided in separate modules in one system.

Further, in the embodiment, RFID is used for recognition of the reagent container, however, not limited to that. The recognition method is feasible using other means including barcodes and IC chips.

FIG. 2 shows a flow at automated replacement of the reagent container.

In the apparatus, in advance, remaining amounts of the reagent containers during use to be recognized as times of reagent replacement by the apparatus are set with respect to all items or with respect of each item (step S1). In this regard, the remaining amount may be a volume, a number of remaining tests, a number of days after installation, or an expiration date. Further, as the way of registration, an operator may enter it in the apparatus or on a screen of another information system than the apparatus, or an ID (e.g. RFID or barcode) previously associated with the reagent container may be read and set.

If the remaining amount of the reagent is equal to or less than a preset value during the analysis by the apparatus (step S2), in other words, if the apparatus recognizes the remaining amount of the reagent equal to or less than the preset value (step S3), the apparatus stops an item analysis for a time required in advance for replenishment of a new reagent container from the second reagent storage to the first reagent disc (step S4). From the spare time cycle, with a spare time cycle of the final reagent dispensing time generated after a certain time (pause cycle of reagent suction), dispensing of the sample and the first reagent is stopped again and reagents are carried in and the amounts of reagents are confirmed during the spare time cycles without dispensing of the sample and the reagent (step S5). Then, after the reagent replacement is performed, the analysis is restarted (step S6).

The temporary stop of the analysis in FIG. 2 corresponds to the time of the spare time cycle and an empty reaction container with which no analysis is made exists, and here, the expression of the temporary stop of the analysis is used. Note that, with respect to the reagent that has been ejected to the reaction container, the analysis is continued even in the temporary stop period.

The cycle necessary for the reagent container replenishment differs from apparatus to apparatus. Further, confirmation of the amount of reagent, the opening and closing of the lid of the reagent container, punching a hole of the reagent container, etc. may be performed until the spare time cycle of the final reagent dispensing is generated or included in the cycle necessary for the reagent container replenishment. When the reagent is ejected after the sample is ejected, a cycle without a need of ejection of the reagent is generated due to existence of the empty reaction container to which no sample is ejected. In other words, a cycle without a need of suction of the reagent from the reagent container of the reagent disc by the reagent dispensing mechanism (non-operation time) is generated. The reagent container replacement (carry-in) is performed at the time. After the reagent container is carried in the apparatus, necessary checks are performed. Without an alarm or the like, the analysis using the reagent of the carried-in reagent container is continuously restarted.

FIG. 3 shows an operation example including a reagent container carry-in schedule.

In an apparatus assumed in FIG. 3, there are a dispensing mechanism that ejects a first reagent (R1) and a dispensing mechanism that ejects a second reagent (R2) as reagents used for items A, B, and a two-reagent system measurement method of dispensing the first reagent in a cycle immediately after sample dispensing (S) (i.e., one cycle after the sample dispensing) and dispensing the second reagent after six cycles from the sample dispensing is applied to the apparatus. Further, for the simpler explanation, regarding the measurement items, only the two items of the items A, B for which a reagent for 100 tests is loaded for each container are alternately measured, setting of scheduling carry-in of the reagent container when the number of remaining tests for the item A is equal to or less than five (X in the drawing) and stopping sample dispensing at every other five cycles (Y in the drawing) until the reagent container for the item A is carried in the apparatus is assumed. The Y is set for creating spare time cycles for the second reagent at regular intervals so that the reagent container may be carried in immediately after the number of remaining tests for the item A becomes zero if how long until the number of remaining test for the item A becomes zero is unknown. The setting is particularly effective for the case of an item at a lower frequency of measurements. The condition is on the assumption that there is a vacant position within the first reagent disc, and not carry-out for automated carrying out of the used-up reagent container.

In the item A, when the number of remaining tests becomes equal to or less than five during analysis (in FIG. 3, item allocated order 5), the spare time cycle is generated at each preset insertion interval (Y) of the spare time cycle. With the spare time cycle, a spare time cycle (pause cycle) for dispersing of the second reagent is generated after a certain time. When the remaining amount of the item A becomes zero or the designated number of remaining tests, the sample dispensing and the first reagent dispensing are stopped with the same cycle as the spare time cycle of the second reagent, a cycle (pause cycle) in which both dispensing nozzles do not suction the reagent is generated in the reagent disc, and the reagent container is carried in during the cycle. Further, after the carry-in of the reagent container, checks of the amounts of reagents of the first reagent and the second reagent are performed using e.g. the first reagent dispensing nozzle.

Next, a control flow formed by further generalization of FIG. 3 will be explained using FIGS. 4 and 5. Here, an example of monitoring the remaining amount of the item A is explained.

The control unit starts an analysis (step S400) at START. In other words, a sample and a reagent corresponding to an item requested for measurement are ejected to the same reaction container and absorbance and scattering luminosity are measured by the photometer. Specifically, the control unit determines whether or not there is the next analysis (step S401). If a determination result at step S401 is NO (namely, there is no next analysis), the analysis is ended and a result is output in wait for the analysis result of the sample that has been ejected to the reaction container. On the other hand, if the determination result at step S401 is YES, absorbance etc. are measured like step S400 (step S402). Then, the control unit determines whether or not the remaining amount of the item A is equal to or less than a threshold value (step S403). If a determination result at step S403 is NO (namely, larger than the threshold value), the processing moves to step S401. On the other hand, if the determination result at step S403 is YES (namely, equal to or less than the threshold value), the processing shifts to a mode of generating a spare time cycle (mode shift). Note that the remaining amount of the item A may be easily grasped because the remaining amount of the reagent is managed by the control unit.

Next, the case of mode shift will be explained. Even when the determination result at step S403 is YES (namely, mode is shifted), the processing goes through the same flow as steps S401 and S402 (steps S404 and S405). Then, the control unit determines whether or not the remaining amount of the item A is zero (step S406). If a determination result at step S406 is YES (namely, the remaining amount of the item A is zero), reagent carry-in preparation is started and this will be described later. On the other hand, if the determination result at step S406 is NO (namely, not zero), the control unit determines whether or not an a-cycle elapses from step S403 next (step S407). Note that the a-cycle here corresponds to Y in FIG. 3. If a determination result at step S407 is NO (namely, it does not elapse), the processing returns to step S404. Further, if the determination result at step S407 is YES (namely, it elapses), a spare time cycle is generated (step S408). The spare time cycle refers to a cycle in which, even when there is an analysis target sample, the sample is intentionally not ejected to the reaction container. Through the series of flow of steps S404 to S408, one spare time cycle is generated in the a-cycle. Note that, at step S406, whether or not the remaining amount of the item A is zero is determined, however, the threshold value is not necessarily zero, but a threshold value smaller than the threshold value at step S403 may be used as the determination criterion at step S406. Further, a plurality of spare time cycles may be continuously generated in the a-cycle, however, one cycle is desirable for prevention of deterioration in processing power.

Next, a flow after generation of the spare time cycle will be explained. Even when the spare time cycle is generated by the processing at step S408, the processing goes through the same flow as steps S404 to S406 (steps S409 to S411). Then, the control unit determines whether or not a b-cycle elapses from step S408 next (step S412). Note that the b-cycle here also corresponds to Y in FIG. 3. If a determination result at step S412 is NO (namely, it does not elapse), the processing returns to step S409. Further, if the determination result at step S412 is YES (namely, it elapses), the processing returns to step S408 and a spare time cycle is generated (step S408). In addition to the steps S409 to S401, through the series of flow of step S408, one spare time cycle is generated in the b-cycle until the remaining amount of the item A becomes zero.

Note that the a-cycle and the b-cycle are separated because "a" as the time when the spare time cycle is first generated is arbitrary, although the explanation is made in the same number of cycles in FIG. 2, but they are not necessarily the same. On the other hand, the b-cycle depends on the apparatus mechanisms. This is because there are the dispensing mechanism of ejecting the first reagent and the dispensing mechanism of ejecting the second reagent, and the time when the second reagent is ejected is after the predetermined cycles elapse from the time when the first reagent is ejected. Accordingly, the number of cycles or a divisor of the number of cycles is set as "b", and thereby, a cycle in which both the first reagent and the second reagent are not ejected (pause cycle) may be generated at regular intervals. The remaining amount may not be zero and a threshold value smaller than the threshold value at step S403 may be used as the determination criterion at step S411 as described above and a plurality of spare time cycles may be continuously generated in the b-cycle, however, one cycle is desirable for prevention of deterioration in processing power.

Next, a flow when the determination results at steps S406, S411 are YES, namely, after the remaining amount of the item A becomes zero will be explained using FIG. 5. If the determination results at steps S406, S411 are YES (the remaining amount of the item A becomes zero), the control unit gives an instruction to start reagent carry-in preparation to the reagent container carry-in mechanism (step S413). Here, the reagent carry-in preparation refers to a preparation operation of grasping a reagent container containing the same kind of reagent as the reagent corresponding to the item A and carrying the grasped reagent container close to the reagent disc by the reagent container carry-in mechanism. Depending on the performance of the reagent container carry-in mechanism, the preparation operation takes time of about three cycles to six cycles. Further, after the instruction of processing at step S413 (reagent input preparation start), the processing goes through the same flow as steps S401 and S402 (steps S414 and S415). Then, the control unit determines whether or not the reagent carry-in preparation has been completed and whether or not the next cycle is a reagent ejection pause cycle in which both the first reagent and the second reagent are not ejected (step S416). If a determination result is YES, the reagent container waiting close to the reagent disc is carried in to a vacant position of the reagent disc (step S419). That is, the reagent container is carried in the reagent ejection pause cycle immediately after the completion of the reagent carry-in preparation. Regarding the carry-in, the carry-in may be completed in one cycle. On the other hand, if the determination result at step S416 is NO (namely, the carry-in preparation has not been completed or the next cycle is not the reagent ejection pause cycle), the control unit makes the same determination as step S412 and controls whether or not to generate a spare time cycle (steps S417, S418). That is, if the determination result at step S416 is YES, a spare time cycle is generated (step S418) and the processing returns to step S414. Further, if the determination result at step S416 is NO, the processing returns to step S414. Through the flow, the spare time cycle is generated once in the b-cycle at regular intervals until the condition at S416 is satisfied, and the reagent ejection pause cycle is continuously generated at regular intervals. If the carry-in of the reagent container is completed, after a check of the amount of reagent is performed (step S420), the processing returns to step S401 and the analysis is continued.

Next, the check of the amount of reagent will be explained. The check of the amount of reagent refers to an operation of determining whether or not the reagent container having a sufficient amount of reagent has been carried in. For example, the reagent dispensing nozzle is moved downward into the reagent container by a predetermined amount, suction operation is performed, and whether or not the predetermined amount of reagent is inside is checked by monitoring pressure at the suction operation. If the amount of reagent is not sufficient, various problems such that a normal analysis result is not obtained arise, and the check must be done. To eliminate the analysis delay of the item A, it is desirable to make the check as quickly as possible after the reagent container is carried in. Accordingly, in FIG. 3, the check is performed in the 17th and 18th cycles immediately after the 16th cycle of the reagent container carry-in. Further, FIG. 3 shows the example of the reagent container in which the container for the first reagent and the container for the second reagent are integrated carried in the reagent disc, and the checks are performed for both containers. Generally, the dispensing mechanism for the first reagent is not used for the second reagent in the container for the second reagent, however, in order to make the checks as quickly as possible, it is desirable to make not only the check of the amount of reagent of the first reagent but also the check of the amount of reagent of the second reagent using the dispensing mechanism of ejecting the first reagent.

If the check of the amount of reagent of the second reagent is performed using the dispensing mechanism of ejecting the second reagent, one cycle is used for the check of the amount of reagent, and it is necessary to generate a spare time cycle in which the sample is not ejected. However, even when the spare time cycle is generated, a substantial number of cycles are necessary for the spare time cycle to reach the ejection position of the second reagent, and the manner may lack promptness of checks and may cause reduction in processing power. Note that, before the spare time cycle reaches the ejection position of the second reagent, the second reagent should be ejected to the sample that has been ejected to the reaction container and it is impossible to make the checks. On the other hand, when this is performed using the dispensing mechanism of ejecting the first reagent, the empty reaction container containing no sample reaches the ejection position of the first reagent in the next cycle to the generation of the spare time cycle, and it is possible to check the container for the second reagent immediately after the generation of the spare time cycle. To continuously make checks on the container for the first reagent and the container for the second reagent for promptness of the checks, as shown in FIG. 3, it is desirable to generate the cycle of reagent carry-in and the next cycle as spare time cycles in which the sample is not ejected.

As above, the explanation is made on the control by the control unit according to the invention, when the remaining amount of a reagent corresponding to a predetermined item becomes equal to or less than a threshold value, of generating a pause cycle of reagent suction in which the reagent dispensing mechanism does not suction the reagent from inside of the reagent container of the reagent disc at regular intervals and automatically carrying the reagent container containing the same kind of reagent as the reagent corresponding to the predetermined item in the reagent disc by the reagent container carrying mechanism in the pause cycle. According to the example in FIGS. 4 and 5, one spare time cycle is generated in the b-cycle, and thereby, one cycle of the pause cycle of reagent suction may be generated at regular intervals. Further, in the pause cycle, the reagent container may be automatically carried in by the reagent container carrying mechanism. One spare time cycle is inserted in the b-cycle, and thereby, period processing power becomes lower after shift to the mode and before the remaining amount is zero or carry-in preparation of the reagent container having a predetermined remaining amount is triggered. However, the pause cycle is generated at regular intervals, and the reagent container may be carried in a short time from the triggered time. Further, the threshold value of the mode shift and the value of "b" are set according to the frequency of use of the reagent, and thereby, the reduction in processing power may be minimized. In addition, because of the automatic carry-in by the reagent container carrying mechanism, the time taken for carry-in is a short time and it is not necessary for the user to attend the reagent carry-in, and the analysis may be continued. For convenience of explanation, in FIG. 3, the example in which the times of the ejection of the first reagent and the ejection of the second reagent are separated by five cycles is explained, however, depending on the apparatus, the times are separated by thirty or more cycles. Particularly, the larger the number of separating cycles, the more effective shortening of the time taken for carry-in.

Further, in FIG. 4, the example in which the determination criteria at steps S406 and S411 are provided is explained. As a modified example, without the determination criteria, the reagent carry-in preparation (step S413) may be performed based on the determination at step S403. However, a certain time is taken for generation of the pause cycle, and it is desirable to set a larger threshold value than the threshold values (steps S406, S411) as conditions truly requiring reagent carry-in as a threshold value of shift to the processing power reduction mode. That is, it is desirable to generate the pause cycle at regular intervals until the threshold value becomes smaller than the threshold value at step S404 or zero, and then, carry in the reagent container. Thereby, when the condition truly requiring reagent carry-in is satisfied, the reagent may be promptly carried in.

Furthermore, it is desirable to set the frequency of generation of the phase cycle (e.g. once in the b-cycle) to be longer than the number of cycles for the reagent container carrying mechanism to carry the reagent container from the reagent storage to the reagent disc. This is because the frequency of generation of the phase cycle is the same as the frequency of generation of the spare time cycle in which the sample is not ejected, and generation of the spare time cycle causing the reduction in analysis power may be suppressed during carriage of the reagent container.

Further, in FIGS. 4, 5, attention is focused on the item A, and, regarding the item B, the reagent container may be carried in according to the same flow. Note that the period of the reduced processing power is made shorter depending on the frequency of use, and it is preferable to provide a display screen by which the threshold value and the frequency of generation of the pause cycle can be set in response to the kind of reagent.

Furthermore, in consideration of two or more different reagents, the processing can be shifted to a mode in which the processing power is reduced when the respective amounts of reagents become equal to or less than the threshold values. In this case, according to the example in FIGS. 4, 5, the pause cycle is generated twice during several cycles, and the processing power may be lower more than necessary. In this case, it is desirable not to generate one pause cycle, but to generate the other pause cycle. Further, similarly, if the set frequencies of generation are the same, according to the example in FIGS. 4, 5, the pause cycle may be generated twice during several cycles. In this case, it is desirable for the control unit to adjust and control "a" of the step S407 so that the pause cycle may be generated in the same cycle.

Note that, in the embodiment, the carry-in to the reagent disc is mainly explained, and, in the case where the reagent container should be carried out from the reagent disc such that there is no vacant position for carrying in the reagent container, the operation may be automatically performed by the reagent container carrying mechanism using the pause cycle. In this case, the reagent container may be carried out in one pause cycle and the reagent container may be carried in another pause cycle. Further, in the embodiment, the form of ejecting the first reagent after the sample is explained, and the embodiment may be similarly applied to the form of ejecting the first reagent before the sample as long as a pause cycle in which the reagent suction is paused is provided and the control of carrying in the reagent container at the time is performed.

As above, the embodiment of this application is explained. According to the invention, when replacement of the reagent container is necessary, under a situation that the analysis of the apparatus should be stopped, the analysis stop period of the apparatus is minimized without the operation by the operator, and thereby, operational efficiency may be improved.

Advantageous effects in the embodiment having the above described configuration will be explained.

The number of operators in a clinical site such as clinical laboratory technologists is minimized with the trend of medical cost reduction, single technologist is extremely busy undertaking a plurality of practices. The busy practices include the maintenance of the apparatus, reagent replacement, calibration curve control, accuracy control, etc. Accordingly, under the present circumstances, reduction of the number of maintenances that the operator should actually perform is required. In an automated analyzing apparatus, after dispensing of a sample, it is necessary to dispense a plurality of reagents in a certain period. In most automated analyzing apparatuses, the first reagent is dispensed and, five minutes later, the next reagent is dispensed. The period is a very important factor in measurement reaction and it is impossible to change the period to dispensing of the second reagent for accurate analysis.

In the clinical site, for reduction of reagent replacement work by the operator, an apparatus having a function of automatically placing reagent containers in locations in which the reagent containers should be placed has been recently launched. When the reagent containers are actually loaded, a certain time is taken for carrying the reagent container from a location for temporary storage to a location in which the container is to be placed. Accordingly, for replenishment work of reagent containers, the operator should wait a time for stopping dispensing of the sample to ejection of the last reagent for the analysis on which a measurement request is currently sent to the apparatus. Particularly, in hours of many test requests, the function is not necessarily a significant function in reality. PTL 1 describes a function of giving an instruction of replenishment of reagent containers to the apparatus in advance, and stopping dispensing for analysis for a designated time and displaying a time till when the reagent containers can be loaded on a screen of the apparatus or the like. The invention enables replenishment of reagent containers without decreasing the original processing power of the apparatus by performing the replenishment work of reagent containers intermittently required with a will of operator's own. However, the work and confirmation by the operator are required and reagent replacement may not be executed until completion of all of the required reagent dispensing with respect to the items that have already been requested for analysis. Therefore, reduction of burden on workers and prompt analyses have not yet realized.

On the other hand, in the embodiment, when a remaining amount of a reagent corresponding to a predetermined item becomes equal to or less than a first threshold value, a pause cycle of reagent suction in which the reagent dispensing mechanism does not suction the reagent from inside of the reagent container of the reagent disc is generated at regular intervals, and the reagent container carrying mechanism automatically carries the reagent container containing the same kind of reagent as the reagent corresponding to the predetermined item in the reagent disc in the pause cycle. Thereby, the remaining amount within the reagent container during use is monitored and dispensing of the sample or the reagent associated with the sample is stopped for a period necessary for carrying the reagent container in a designated location at the time when the remaining amount is an arbitrary set amount, and the analysis stop time of the apparatus for carrying in and out of the reagent container may be minimized.

REFERENCE SIGNS LIST

1 . . . analyzing apparatus, 2 . . . sample disc, 3 . . . sample container, 4 . . . reaction disc, 5 . . . reaction container, 6 . . . sample dispensing mechanism, 7 . . . first reagent disc, 8 . . . reagent container, 9 . . . reagent dispensing mechanism, 10 . . . stirring mechanism, 11 . . . lightsource, 12 . . . multi-wavelength photometer, 13 . . . A/D converter, 14 . . . reaction container cleansing mechanism, 15 . . . dispensing nozzle cleansing mechanism, 16 . . . second reagent storage, 17 . . . reagent container carrying mechanism, 18 . . . communication means, 19 . . . interface, 20 . . . computer, 21 . . . memory means, 22 . . . display unit

The invention claimed is:

1. An automated analyzing apparatus comprising:
a reaction disc on which a reaction container for reaction of a sample and a reagent is mounted;
a light source that applies light to the reaction container;
a photometer that senses the light applied to the reaction container;
a reagent disc on which a first reagent container containing the reagent used for the reaction is placed;
a reagent storage that stores a second reagent container containing the same reagent;
a reagent container carrying mechanism that carries the second reagent container from the reagent storage to the reagent disc;
a reagent dispensing mechanism that suctions the reagent from the first reagent container on the reagent disc and ejects the reagent to the reaction container;
a sample dispensing mechanism that ejects the sample to the reaction container; and
a processor programmed to control the reagent dispensing mechanism and the reagent container carrying mechanism according to a plurality of cycles, in each of which the reagent dispensing mechanism is controlled to suction the reagent from inside of the first reagent container on the reagent disc,
wherein the processor is further programmed to:
repeatedly generate, when a remaining amount of the reagent corresponding to a predetermined item becomes less than or equal to a first threshold value in one of the cycles, a plurality of pause cycles in which the reagent dispensing mechanism does not suction the reagent from inside of the first reagent container on the reagent disc and insert the generated pause cycles at regular intervals from the one of the cycles where the remaining amount of the reagent corresponding to the predetermined item becomes less than or equal to the first threshold value, and
when the remaining amount of the reagent corresponding to the predetermined item becomes zero, carry the second reagent container containing the same reagent corresponding to the predetermined item in from the reagent storage to the reagent disc by the reagent container carrying mechanism in a next one of the pause cycles.

2. The automated analyzing apparatus according to claim 1, wherein the processor is further programmed to, when the remaining amount of the reagent corresponding to the predetermined item has become zero, perform a preparation operation of grasping the second reagent container to be carried in from the reagent storage using the reagent container carrying mechanism, and further carry the second reagent container to the reagent disc in the next one of the pause cycles immediately after completion of the preparation operation.

3. The automated analyzing apparatus according to claim 2, wherein a number of the cycles in each of the regular intervals is longer than a number of the cycles for the reagent container carrying mechanism to carry the second reagent container from the reagent storage to the reagent disc.

4. The automated analyzing apparatus according to claim 1, wherein the reagent dispensing mechanism includes a first reagent dispensing mechanism and a second reagent dispensing mechanism, and the first reagent dispensing mechanism and the second reagent dispensing mechanism do not suction the reagent from the first reagent container in the pause cycle.

5. The automated analyzing apparatus according to claim 1, further comprising:
   a display screen connected to the processor,
     wherein the processor is further programmed to set the first threshold value and set a frequency of generation of the pause cycle for the reagent, and to display the first threshold value and the frequency of generation of the pause cycle.

6. The automated analyzing apparatus according to claim 5, wherein the processor is further programmed to generate the pause cycles when the remaining amount of the reagent corresponding to the predetermined item is less than or equal to the first threshold value and a remaining amount of another reagent different from the reagent corresponding to the predetermined item is less than or equal to a third threshold value.

7. The automated analyzing apparatus according to claim 1, wherein one or more other reagent containers containing other reagents are disposed on the reagent disc in addition to the first reagent container,
   wherein the processor is further programmed to set the first threshold value and set a first frequency of generation of the pause cycles for the reagent corresponding to the predetermined item, and to set a second threshold value and set a second frequency of generation of the pause cycles for a second reagent among the other the reagents on the reagent disc that is different from the reagent corresponding to the predetermined item,
   wherein the processor is further programmed to generate the pause cycles when the remaining amount of the reagent corresponding to the predetermined item is less than or equal to the first threshold value and a remaining amount of the second reagent different from the reagent corresponding to the predetermined item is less than or equal to the second threshold value, and
   wherein the first and second frequencies of the first and second reagents are the same.

* * * * *